United States Patent [19]

Buck

[11] 4,362,713

[45] Dec. 7, 1982

[54] SALTS OF MALEIC ACID COPOLYMERS AS DENTAL PLAQUE BARRIER AGENTS

[75] Inventor: Carl J. Buck, Berkeley Heights, N.J.

[73] Assignee: Johnson & Johnson Products Inc., New Brunswick, N.J.

[21] Appl. No.: 172,496

[22] Filed: Jul. 25, 1980

[51] Int. Cl.$^3$ .................. A61K 7/22; A61K 31/74; A61K 31/19; C08F 30/04

[52] U.S. Cl. .................................. 424/54; 424/49; 424/78; 424/316; 424/317; 433/202; 526/240

[58] Field of Search .................................. 424/49–56, 424/78, 80; 526/240; 433/202

[56] References Cited

U.S. PATENT DOCUMENTS

| | | | |
|---|---|---|---|
| 3,429,963 | 2/1969 | Shedlousky | 424/56 |
| 3,956,244 | 5/1976 | Carpenter et al. | 424/49 |
| 4,138,477 | 2/1979 | Gaffar | 424/52 |
| 4,177,258 | 12/1979 | Gaffar et al. | 424/49 |
| 4,183,914 | 1/1980 | Gaffar et al. | 424/48 |
| 4,238,476 | 12/1980 | Harvey | 424/56 |

FOREIGN PATENT DOCUMENTS 1072413  2/1980  Canada.

OTHER PUBLICATIONS

International Publication No. WO79/00456 – Jul. 26, 1979, PCT application.

*Primary Examiner*—Douglas W. Robinson

[57] ABSTRACT

Compositions and methods for preventing the attachment of dental plaque to the surface of the teeth of mammals comprise certain salts of certain maleic acid copolymers in a pharmaceutically acceptable vehicle and the periodic application thereof to teeth.

6 Claims, No Drawings

SALTS OF MALEIC ACID COPOLYMERS AS DENTAL PLAQUE BARRIER AGENTS

TECHNICAL FIELD

This invention relates to oral hygiene compositions and methods using such compositions to prevent attachment of bacteria to teeth. More particularly, it relates to salts of certain maleic acid copolymers that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Certain hydrophilic alkali metal and ammonium salts of 1:1 copolymers of styrene and maleic acid and 1:1 copolymers of certain linear 1-alkenes and maleic acid have been found to inhibit the deposition of dental plaque onto human teeth when applied from various dentifrice formulations, mouth rinses, or other oral hygiene procedures. While the mechanism of action of the hydrophilic polymer films in retarding plaque deposition is not known with absolute certainty, it is presumed that the films of the anionically-charged polymers deposited on teeth effect a mutual repulsion between the negatively-charged polymer film and the negatively-charged microorganisms in oral fluids responsible for plaque generation. The polymeric carboxylic acid salts of this invention are especially effective as components of dentifrices or other oral hygiene preparations in reducing dental plaque deposition on teeth.

The hydrophilic, polymeric carboxylate salts useful for dental plaque control in accordance with the present invention consist of repeating units selected from the group consisting of structure (A),

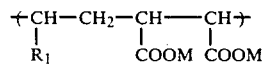
(A)

and structure (B),

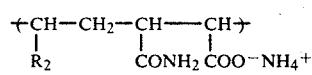
(B)

where $R_1$ is a linear alkyl group of 4 to 12 carbon atoms or a phenyl group, $R_2$ is a linear alkyl group of 4 to 16 carbon atoms or a phenyl group, M is sodium, potassium, or an ammonium ion derived from ammonia, the maleic acid comonomer concentration in said repeating units of structures (A) and (B) is about 50 mole percent, and the molecular weights of the copolymers of structures (A) and (B) are in the range of about 10,000 to about 50,000.

The polymeric alkali metal and ammonium salts of this invention, represented by structures (A) and (B), are either readily available items of commerce or can be prepared from commercially-available polymers, examples being the following:

(1) Scripset ® Resins 500, 501, and 700; the 1:1 styrene/disodium maleate copolymer available from Monsanto Company in a molecular weight of about 50,000:

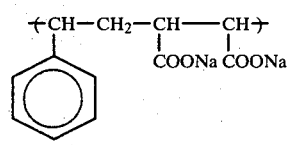

(2) Scripset ® 808 and 720, a 1:1 styrene copolymer of the half amide/half ammonium salt prepared from Scripset ® 520 and available from Monsanto Company,

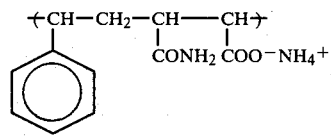

(3) Scripset ® 520, a 1:1 styrene/maleic anhydride copolymer available from Monsanto Company in a range of molecular weights,

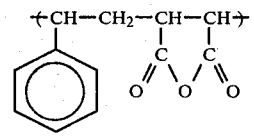

(4) Polyanhydride Resins PA-6, PA-10, PA-14, and PA-18, which are solid 1:1 copolymers of various linear 1-alkenes and maleic anhydride having a molecular weight of about 50,000 and available from Gulf Oil Chemicals Co.,

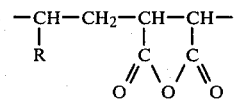

where R=linear alkyl of 4, 8, 12, and 16 carbon atoms.

The salts of the copolymers of this invention are prepared by methods described in the Monsanto Company brochure, #6475, on "The Chemistry of Scripset Resins", and in technical data sheets on the polyanhydride resins, PA-6 and PA-18, provided by Gulf Oil Chemicals Company. The procedure for preparation of polymers of structure (A) involves addition of the maleic anhydride copolymer to aqueous solutions of an alkali metal hydroxide, such as sodium hydroxide and potassium hydroxide, wherein the alkali metal salts of the corresponding maleic acid copolymer are readily produced. The diammonium salts may be prepared by addition of ammonium hydroxide to the corresponding maleic acid copolymers. For preparation of polymers of structure (B), the 1:1 maleic anhydride copolymers are reacted with concentrated aqueous ammonium hydroxide at a pH of about 9 to produce the half amide-ammonium carboxylate polymer. The general synthetic schemes for preparation of the polymers of this invention are outlined in equations (1) to (3):

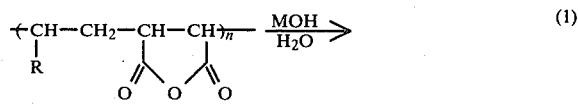

(1)

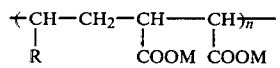

where M = sodium or potassium

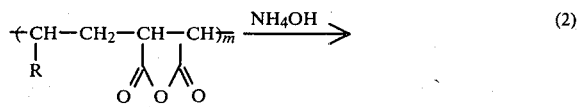

(2)

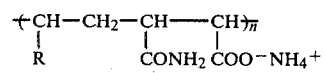

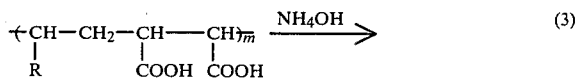

(3)

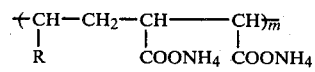

The hydrophilic polymeric salts of this invention are highly effective in reducing the deposition of plaque during in vitro testing. The in vitro test procedure employed for determining the plaque barrier activity of the test materials begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

A particular feature of the 1-alkene/maleic acid salts of of this invention, which appears to govern their effectiveness as agents for the reduction of plaque deposition, is the balance between the hydrophobic and hydrophilic properties of the polymers. The hydrophobic portion in the polymeric repeating units is that derived from the 1-alkene comonomer. The hydrophilic moieties are the carboxylic acid salt groups. In the case of the polymers of structure (A), good plaque barrier properties are obtained when $R_1$ is phenyl or an alkyl group in the 4 to 12 carbon range, the greatest plaque barrier activity being obtained when $R_1$ was butyl or octyl. The disodium salt of the ethylene/maleic acid copolymer (where $R_1$ is hydrogen) and the corresponding salt derived from polyanhydride resin PA-18 (where $R_1$ is hexadecyl) showed no activity in reduction of plaque deposition. These effects of polymer structure, possibly related to the previously mentioned hydrophobic/hydrophilic balance, are shown in Table 1.

TABLE 1

Plaque Barrier Properties of Salts of Maleic Acid Copolymers

| Type Structure | R | % Plaque Reduction |
|---|---|---|
| C | H | 5 |
| C | $C_4H_9$ | 83 |
| C | $C_8H_{17}$ | 78 |
| C | $C_{12}H_{25}$ | 35 |
| C | $C_{16}H_{33}$ | 0 |
| C | Phenyl | 72 |
| D | $C_{16}H_{33}$ | 38 |

EXAMPLE 1

Poly(1-hexene-co-disodium maleate, 1:1)

To a solution of 12.5 g sodium hydroxide and 20.0 g bis(2-ethoxyethyl)ether in 347 ml. water was added 26.0 g of poly(1-hexene-co-maleic anhydride, 1:1) [polyanhydride resin PA-6 (Gulf Oil Chemical Co.)]. The mixture was stirred at about 90°–100° C. for one hour, cooled to room temperature, and the hazy solution added to 1000 ml. 95% ethanol with vigorous stirring. The resultant solids were filtered, washed with ethanol and methanol, and dried to give 35.6 g of poly(1-hexene-co-disodium maleate, 1:1).

EXAMPLE 2

Ammonium Amidate Derivative of Poly(1-octadecene-co-maleic anhydride, 1:1)

Concentrated ammonium hydroxide (14.3 ml.) was added over 30 minutes to a vigorously stirred solution of 10.0 g poly(1-octadecene-co-maleic anhydride, 1:1) [polyanhydride resin, PA-18, Gulf Oil Chemicals Co.] in 25 ml. tetrahydrofuran. After stirring another two hours at room temperature, the thick suspension of solids was diluted with methanol, suction-filtered, and the solids washed further with tetrahydrofuran. The yield of the ammonium amidate derivative was 10.4 g, a white powder showing a melting point of 179°–183° C.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A - Mouthwash Solution

| | |
|---|---|
| Barrier Agent | 0.5-2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B - Mouthwash Solution

| | |
|---|---|
| Plaque Barrier Agent | 0.5-3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C - Abrasive Dentifrice Gel

| | |
|---|---|
| Plaque Barrier Agent | 2.0-10.0% w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |

-continued

| | |
|---|---|
| Sorbitol (humectant) | 10.0 |
| Flavors | 1.0 |
| Deionized Water | q.s. |
| Preservative | 0.05 |
| | 100.0 |

EXAMPLE D - Chewing Gum

| | |
|---|---|
| Plaque Barrier Agent | 1.0-11.0% w/w |
| Gum Base | 21.3 |
| Sugar | 48.5-58.5 |
| Corn Syrup (Baume 45) | 18.2 |
| Flavors | 1.0 |
| | 100.0 |

EXAMPLE E - Nonabrasive Gel Dentifrice

| | |
|---|---|
| Plaque Barrier Agent | 0.05-30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD&C Blue #1 (0.1% aq. soln.) | 0.27 | |
| D&C Yellow #10 (0.5% aq. soln.) | 0.50 | |
| Gelling agent | 18.00 | |
| Glycerol (Humectant) | 20.00 | |
| Cab-O-Sil M5 (Silicon Dioxide) | 1.00 | |
| Plaque Barrier Agent | 5.00 | (dry basis) |
| Flavor | 0.80 | |
| | 100.0 | |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. An oral hygiene composition comprising an effective amount for preventing deposition of dental plaque on teeth of a maleic acid copolymer having repeating units selected from the group consisting of structure (A),

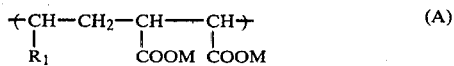

and structure (B),

wherein $R_1$ is a linear alkyl group of 4 to 12 carbon atoms, $R_2$ is a linear alkyl group of 4 to 16 carbon atoms or a phenyl group, and M is sodium, potassium, or an ammonium ion derived from ammonia, the maleic acid comonomer concentration in each of said structures (A) and (B) being about 50 mole percent, the molecular weight of said copolymer being from about 10,000 to about 50,000, in a pharmaceutically acceptable oral hygiene vehicle compatible with said polymer.

2. A method of preventing deposition of dental plaque on teeth comprising periodically applying to the teeth a composition of claim 1.

3. The method of claim 2 wherein said composition is applied from about 1 to about 3 times per day.

4. The composition of claim 1 which comprises a copolymer having repeating units of structure A wherein $R_1$ is a linear alkyl groups of 4 to 8 carbon atoms.

5. The composition of claim 1 which comprises a copolymer having repeating units of structure B wherein $R_2$ is a linear alkyl group of about 16 carbon atoms.

6. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *